(12) United States Patent
Gavade (10) Patent No.: US 11,883,608 B2
(45) Date of Patent: Jan. 30, 2024

(54) PEDIATRIC CATHETER SYSTEM AND RELATED DEVICES AND METHODS

(71) Applicant: Becton, Dickinson and Company, Franklin Lakes, NJ (US)

(72) Inventor: Pravin Bhagavant K. Gavade, Karnataka (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 201 days.

(21) Appl. No.: 17/207,463

(22) Filed: Mar. 19, 2021

(65) Prior Publication Data

US 2021/0299403 A1    Sep. 30, 2021

Related U.S. Application Data

(60) Provisional application No. 63/002,938, filed on Mar. 31, 2020.

(51) Int. Cl.
  *A61M 25/00* (2006.01)
  *A61M 25/06* (2006.01)

(52) U.S. Cl.
  CPC ...... *A61M 25/0054* (2013.01); *A61M 25/007* (2013.01); *A61M 25/0097* (2013.01);
  (Continued)

(58) Field of Classification Search
  CPC .......... A61M 25/0606; A61M 25/0625; A61M 25/0662; A61M 25/0693; A61M 25/0637;
  (Continued)

(56) References Cited

U.S. PATENT DOCUMENTS

| 2,937,643 A | 5/1960 | Elliot |
| 2006/0150742 A1* | 7/2006 | Esnouf .................... G01L 7/063 73/716 |

(Continued)

FOREIGN PATENT DOCUMENTS

| EP | 1606007 | 12/2005 |
| JP | 4689922 | 7/2003 |

(Continued)

OTHER PUBLICATIONS

Matthew W. Linakis, Jessica K. Roberts, Anita C. Lala, Michael G. Spigarelli, Natalie J. Medlicott4, David M. Reith, Robert M. Ward, Catherine M. T. Sherwin1, "Challenges Associated with Route of Administration in Neonatal Drug Delivery", Aug. 6, 2015, CrossMark, pp. 185-196 (Year: 2015).*

*Primary Examiner* — Kami A Bosworth
*Assistant Examiner* — Antarius S Daniel
(74) *Attorney, Agent, or Firm* — Kirton McConkie; Whitney Blair; Kevin Stinger (57) ABSTRACT

A catheter system may include a catheter adapter, which may include a distal end, a proximal end, and a lumen extending through the distal end of the catheter adapter and the proximal end of the catheter adapter. The catheter system may include a concertinaed tube, which may include a distal end coupled to the proximal end of the catheter adapter. The concertinaed tube may be disposed in a collapsed position and movable between the collapsed position and an expanded position. The catheter system may include a luer connector, which may be coupled to a proximal end of the concertinaed tube. The catheter system may include a needle assembly, which may include a needle hub and an introducer needle extending distally from the needle hub. The concertinaed tube and the luer connector may be disposed within the needle hub.

20 Claims, 12 Drawing Sheets (52) U.S. Cl.
CPC .... *A61M 25/0606* (2013.01); *A61M 25/0637* (2013.01); *A61M 25/0693* (2013.01); *A61M 2205/586* (2013.01); *A61M 2205/75* (2013.01)

(58) Field of Classification Search
CPC ............ A61M 25/0097; A61M 25/007; A61M 25/0054; A61M 25/2025; A61M 25/0253; A61M 25/0681
See application file for complete search history.

(56) References Cited

U.S. PATENT DOCUMENTS

| | | | | |
|---|---|---|---|---|
| 2013/0267845 | A1* | 10/2013 | Howle | A61M 25/007 |
| | | | | 600/432 |
| 2014/0364809 | A1 | 12/2014 | Isaacson et al. | |
| 2016/0158523 | A1 | 6/2016 | Helm | |
| 2016/0331365 | A1* | 11/2016 | Chu | D05B 85/12 |
| 2016/0354539 | A1* | 12/2016 | Tan | A61M 5/158 |
| 2016/0361519 | A1* | 12/2016 | Teoh | A61M 25/0606 |
| 2017/0120011 | A1* | 5/2017 | Burkholz | A61M 5/158 |
| 2017/0120014 | A1* | 5/2017 | Harding | A61M 25/0606 |
| 2020/0023166 | A1 | 1/2020 | Burkholz et al. | |
| 2020/0046948 | A1* | 2/2020 | Burkholz | A61B 5/150732 |
| 2020/0316313 | A1* | 10/2020 | Ishida | A61M 5/3293 |

FOREIGN PATENT DOCUMENTS

| | | | | |
|---|---|---|---|---|
| WO | 2011/044296 | | 4/2011 | |
| WO | WO-2011044296 A1 * | | 4/2011 | ........ A61M 25/0021 |

\* cited by examiner

FIG. 6D

PEDIATRIC CATHETER SYSTEM AND RELATED DEVICES AND METHODS

RELATED APPLICATIONS

This application claims the benefit of U.S. Provisional Patent Application No. 63/002,938, filed on Mar. 31, 2020, entitled PEDIATRIC CATHETER SYSTEM AND RELATED DEVICES AND METHODS, which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Because of poor vein pressure, needle placement confirmation is a challenge in a pediatric patient, which may include an infant. Also, catheter extravasation can occur due to a small size of a vein of the pediatric patient, resulting in medication escaping into surrounding tissue. In an integrated catheter assembly, an extension tube is integrated into and extends from a side port of a catheter adapter. The extension tube may be used for blood draw and/or infusion. When the catheter assembly is integrated, several additional challenges are presented with respect to the pediatric patient. First, multiple bandages are generally used to secure the extension tube to skin of the pediatric patient, which can make the pediatric patient uncomfortable and/or lead to removal or dislodgement of the integrated catheter assembly by the pediatric patient. Second, the integrated catheter assembly often needs pre-priming with more flush volume due to increased dead space within the integrated catheter assembly. Third, a weight and size of the integrated catheter assembly can be difficult for the pediatric patient to support.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems and related devices and methods. In particular, the present disclosure relates to a pediatric catheter system and related devices and methods. In some embodiments, a catheter system may include a catheter adapter, which may include a distal end, a proximal end, and a lumen extending through the distal end of the catheter adapter and the proximal end of the catheter adapter. In some embodiments, the catheter adapter may include one or more push tabs. In some embodiments, the catheter adapter may include a first wing and/or a second wing. In some embodiments, the first wing and the second wing may extend outwardly from opposite sides of a body of the catheter adapter.

In some embodiments, the catheter system may include a concertinaed tube, which may include a distal end coupled to the proximal end of the catheter adapter and/or disposed in a collapsed position. In some embodiments, the concertinaed tube may be movable between the collapsed position and an expanded position. In some embodiments, in response to the concertinaed tube moving between the expanded position and the collapsed position, a length of the concertinaed tube may be reduced by 50% to 70%, inclusive. In some embodiments, the catheter system may have a length of about 75 mm or less.

In some embodiments, the catheter system may include a luer connector, which may be coupled to a proximal end of the concertinaed tube. In some embodiments, the luer connector may include a cannula and a slit septum surrounding the cannula. In some embodiments, the cannula may include one or more openings. In some embodiments, a proximal end of the slit septum may form a seal with an inner surface of the luer connector, which may reduce a dead space within the luer connector. In some embodiments, the catheter system may be flushed with only about 2.0 mL due to the reduced dead space. In some embodiments, the catheter system may be flushed with between 2 and 2.5 mL, inclusive.

In some embodiments, the catheter system may include a needle assembly, which may include a needle hub and an introducer needle extending distally from the needle hub. In some embodiments, the concertinaed tube and the luer connector may be disposed within the needle hub. In some embodiments, a proximal end of the needle hub may include a flashback chamber in fluid communication with a lumen of the introducer needle. In some embodiments, the needle hub may include a hydrophobic filter proximate the flashback chamber.

In some embodiments, the catheter system may include a catheter extending from the distal end of the catheter adapter. In some embodiments, a distal end of the catheter may include one or more side holes. In some embodiments, the catheter may be configured to provide a flow rate of 1.235 mL/hr to 5.400 mL/hr, inclusive.

In some embodiments, the catheter system may include a passive safety mechanism, such as, for example, a passive needle safety clip. In some embodiments, the passive needle safety clip may be disposed within the needle hub between the luer connector and a proximal end of the needle hub. In some embodiments, the introducer needle may extend through the passive needle safety clip. In some embodiments, the passive needle safety clip may include a proximal opening. In some embodiments, an outer surface of the introducer needle may include a feature. In some embodiments, an outer diameter of the feature may be greater than a diameter of the proximal opening such that the feature is prevented from moving proximal to the proximal opening.

In some embodiments, a method may include inserting a catheter system into vasculature of a patient. In some embodiments, the method may include removing the needle assembly from the catheter system inserted within the vasculature of the patient. In some embodiments, after removing the needle assembly from the catheter system, the method may include moving the concertinaed tube from the collapsed position to the expanded position.

In some embodiments, after moving the concertinaed tube from the collapsed position to the expanded position, the method may include coupling an extension set to the proximal end of the concertinaed tube. In some embodiments, the method may include administering a drug to the patient through the extension set.

In some embodiments, after moving the concertinaed tube from the collapsed position to the expanded position, the method may include coupling an infusion device to the proximal end of the concertinaed tube. In some embodiments, a priming step may be eliminated. In some embodiments, no priming of the catheter system may occur prior to inserting the catheter system into the vasculature of the patient. In some embodiments, a single hand may be used to insert the catheter system into the vasculature of the patient. In some embodiments, in response to removing the needle assembly from the catheter system inserted within the vasculature of the patient, a drag force on the introducer needle may be less than about 1.1 N.

It is to be understood that both the foregoing general description and the following detailed description are examples and explanatory and are not restrictive, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
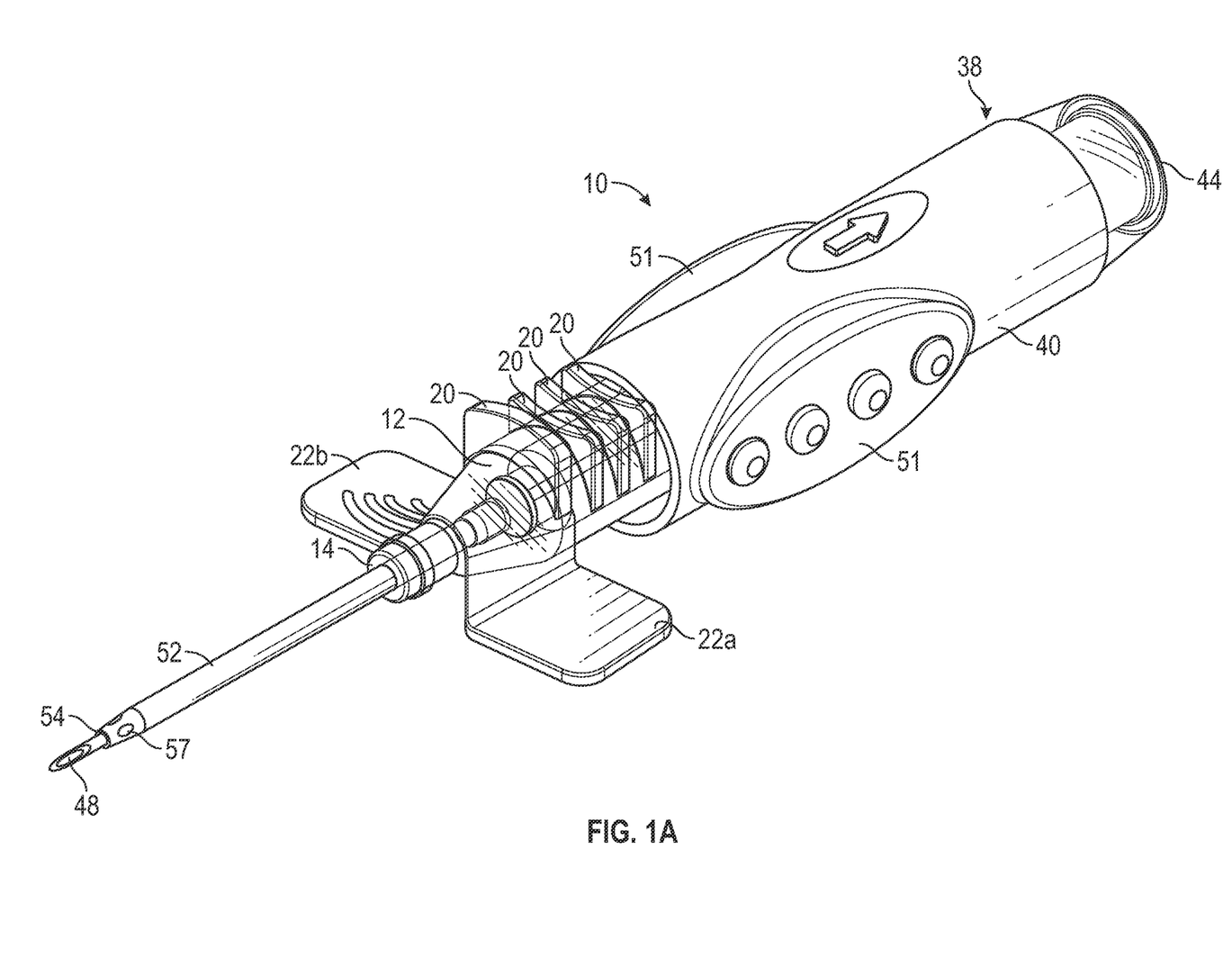
FIG. 1A is an upper perspective view of an example catheter system, according to some embodiments.
Figure 1B:
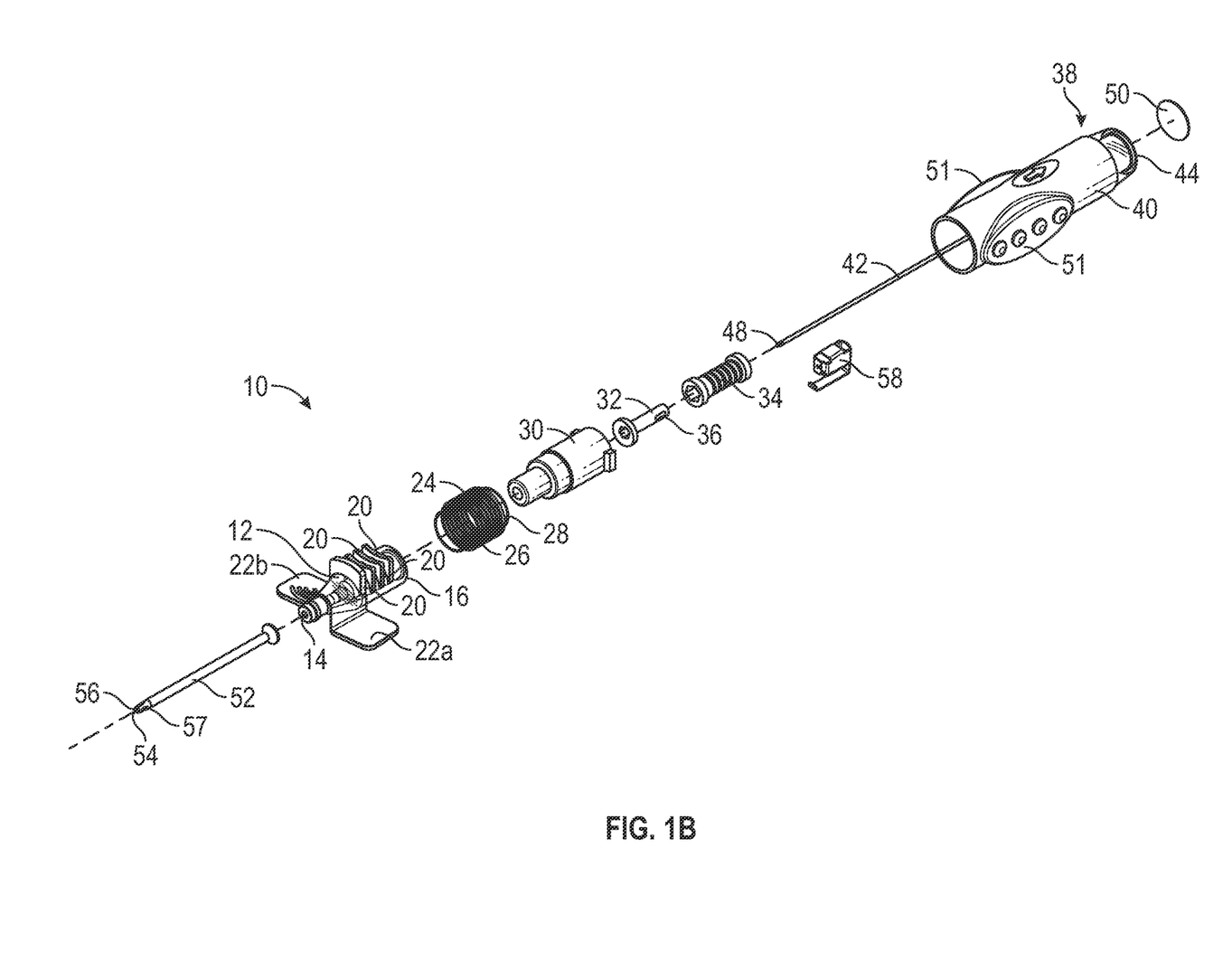
FIG. 1B is an exploded view of the catheter system of FIG. 1A, according to some embodiments.
Figure 1C:
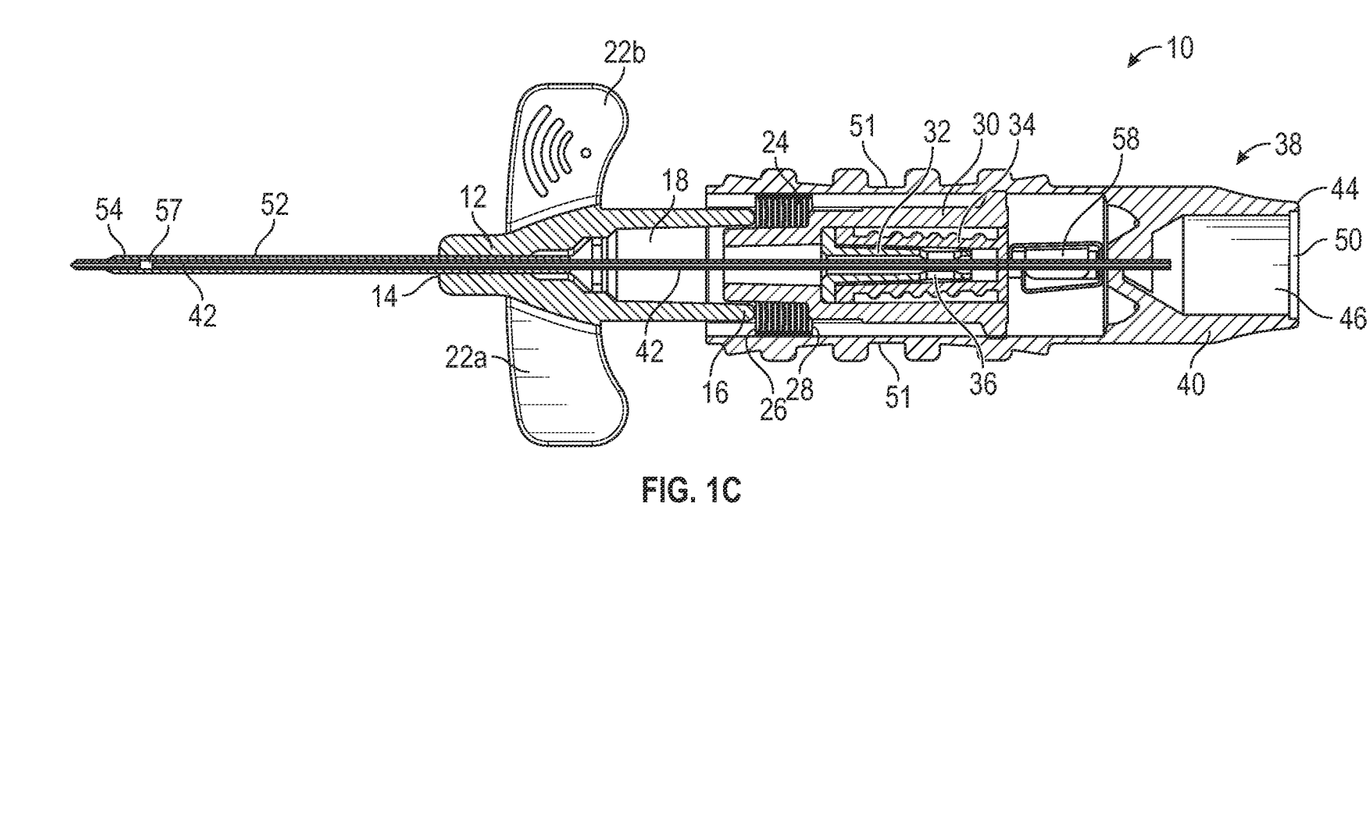
FIG. 1C is a cross-sectional view of the catheter system of FIG. 1A, according to some embodiments.

Referring now to FIGS. 1A-1C, in some embodiments, a catheter system 10 may include a catheter adapter 12, which may include a distal end 14, a proximal end 16, and a lumen 18 extending through the distal end 14 of the catheter adapter 12 and the proximal end 16 of the catheter adapter 12. In some embodiments, the catheter adapter 12 may include one or more push tabs 20. In some embodiments, the catheter adapter 12 may include a first wing 22a and/or a second wing 22b. In some embodiments, the first wing 22a and the second wing 22b may extend outwardly from opposite sides of a body of the catheter adapter 12.

In some embodiments, the catheter system 10 may include a concertinaed tube 24, which may include a distal end 26 coupled to the proximal end 16 of the catheter adapter 12 and/or disposed in a collapsed position, as illustrated in FIG. 1C, for example. In some embodiments, the concertinaed tube 24 may be movable between the collapsed position and an expanded position. In some embodiments, in response to the concertinaed tube 24 moving between the expanded position and the collapsed position, a length from the distal end 26 to a proximal end 28 of the concertinaed tube 24 may be reduced by 50% to 70%, inclusive. In some embodiments, in response to the concertinaed tube 24 moving between the expanded position and the collapsed position, a length from the distal end 26 to a proximal end 28 of the concertinaed tube 24 may be reduced by about 60%.

In some embodiments, the catheter system 10 may include a luer connector 30, which may be coupled to the proximal end 28 of the concertinaed tube 24. In some embodiments, the luer connector 30 may include a cannula 32 and a slit septum 34 surrounding the cannula 32. In some embodiments, the cannula 32 may include one or more openings 36.

In some embodiments, the catheter system 10 may include a needle assembly 38, which may include a needle hub 40 and an introducer needle 42 extending distally from the needle hub 40. In some embodiments, the concertinaed tube 24 and the luer connector 30 may be disposed within the needle hub 40. In some embodiments, a proximal end 44 of the needle hub 40 may include a flashback chamber 46 in fluid communication with a lumen of the introducer needle 42, which may extend through a sharp distal tip 48 of the introducer needle 42. In some embodiments, the needle hub 40 may include a hydrophobic filter 50 proximate the flashback chamber 46. In some embodiments, the hydrophobic filter 50 may be welded at the proximal end 44 of the needle hub 40 and may reduce or eliminate a need for priming the catheter system 10 prior to insertion into the vasculature. In some embodiments, the hydrophobic filter 50 may have an air flow capacity between 5 cc/min and 50 cc/min, inclusive, when subjected to 1.0±0.1 PSI.

In some embodiments, the needle hub 40 may include one or more side grips 51. In some embodiments, the side grips 21 may include generally oval-shaped surfaces, which may be generally planar and/or dish-shaped. In some embodiments, the generally oval-shaped surfaces may include one or more protrusions, which may be aligned with a longitudinal axis of the needle hub 40 or in another configuration. In some embodiments, the push tabs 20 and/or one or more other features (such as, for example, the side grips 51) may facilitate multiple insertion or removal techniques, such as, for example, use of a single hand to insert the catheter system 10 into the vasculature of the patient and/or removal the needle assembly 38 from the catheter system 10.

In some embodiments, the catheter system 10 may include a catheter 52 extending from the distal end 14 of the catheter adapter 12. In some embodiments, a distal end 54 of the catheter 52 may include a distal opening 56 aligned with a longitudinal axis of the catheter 52. In some embodiments, the catheter 52 may include one or more side holes 57, which may provide additional fluid paths into and out of the catheter 52. In some embodiments, the catheter 52 with the one or more side holes 57 may be configured to provide a flow rate of about 1.235 mL/hr to about 5.400 mL/hr, inclusive. In some embodiments, the catheter system 10 may have a length of about 75 mm. In some embodiments, the length of the catheter system may extend from a distal-most portion of the distal end 54 of the catheter 52 to a proximal-most portion of the proximal end 44 of the needle hub 40.

In some embodiments, the catheter system 10 may include a passive safety mechanism, such as, for example, a passive needle safety clip 58. In some embodiments, the passive needle safety clip 58 may be disposed within the needle hub 40 between the luer connector 30 and the proximal end 44 of the needle hub 40.

In some embodiments, the catheter system 10 may reduce foot prints on a body of a pediatric patient. In some embodiments, the catheter system 10 may be compact and may not include an extension tube extending from the catheter adapter 12, which may reduce a number of bandages used to secure the catheter system 10 to skin of the patient and may eliminate a need for clamping. In some embodiments, the catheter system 10 may be straight and/or closed.

Figure 2A:
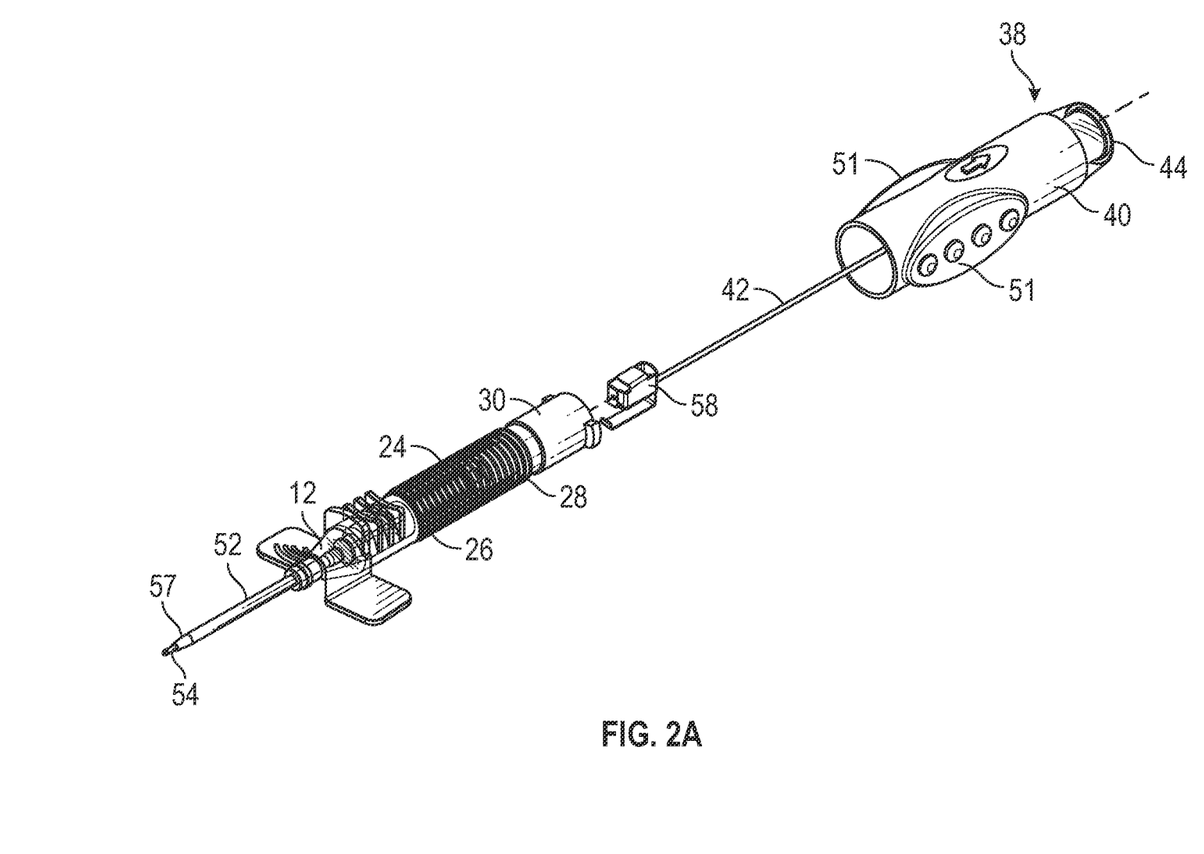
FIG. 2A is an upper perspective view of the catheter system of FIG. 1A, illustrating an example needle assembly removed from the catheter system, according to some embodiments.
Figure 2B:
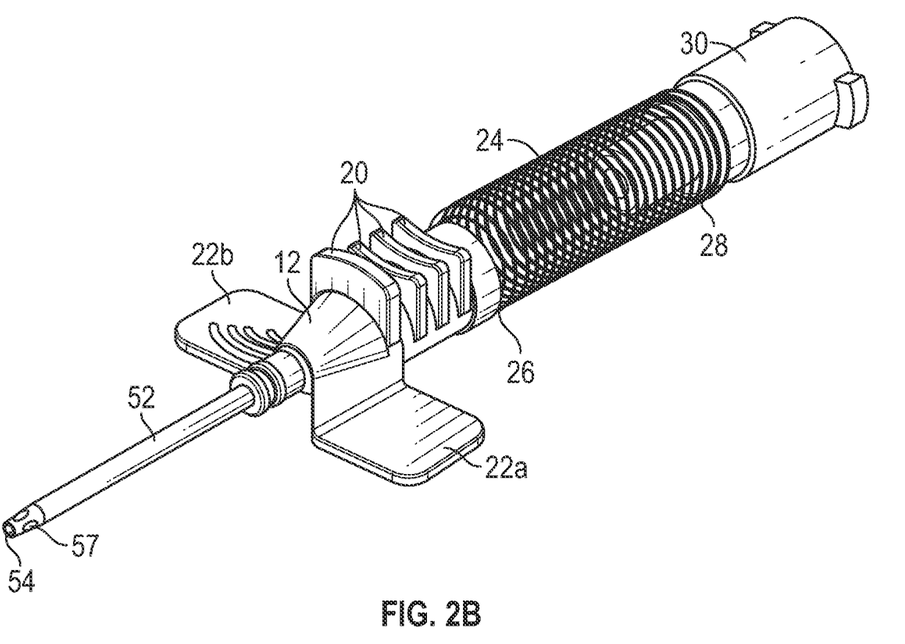
FIG. 2B is an upper perspective view of the catheter system of FIG. 1A, illustrating the needle assembly removed and an example concertinaed tube in an expanded position, according to some embodiments.

Referring now to FIGS. 2A-2B, in some embodiments, a method may include inserting the catheter system 10 into vasculature of a patient. In some embodiments, in response to the introducer needle 42 being inserted into the vasculature, blood may flow through the introducer needle 42 and into the flashback chamber 46, where the blood may be observed by the clinician. In some embodiments, the method may include removing the needle assembly 38 from the catheter system 10 inserted within the vasculature of the patient. In some embodiments, the needle assembly 38 may be disposed of after removed from the catheter system 10.

In some embodiments, a priming step may be eliminated. In some embodiments, no priming of the catheter system 10 may occur prior to inserting the catheter system 10 into the vasculature of the patient. In some embodiments, in response to removing the needle assembly 38 from the catheter system 10 inserted within the vasculature of the patient, a drag force on the introducer needle 42 may be less than about 1.1 N.

In some embodiments, in response to removing the needle assembly 38 from the catheter system, the sharp distal tip 48 of the introducer needle 42 may be shielded within the passive needle safety clip 58. In some embodiments, after removing the needle assembly 38 from the catheter system 19, the method may include moving the concertinaed tube 24 from the collapsed position to the expanded position, as illustrated, for example, in FIG. 2B.

Figure 3A:
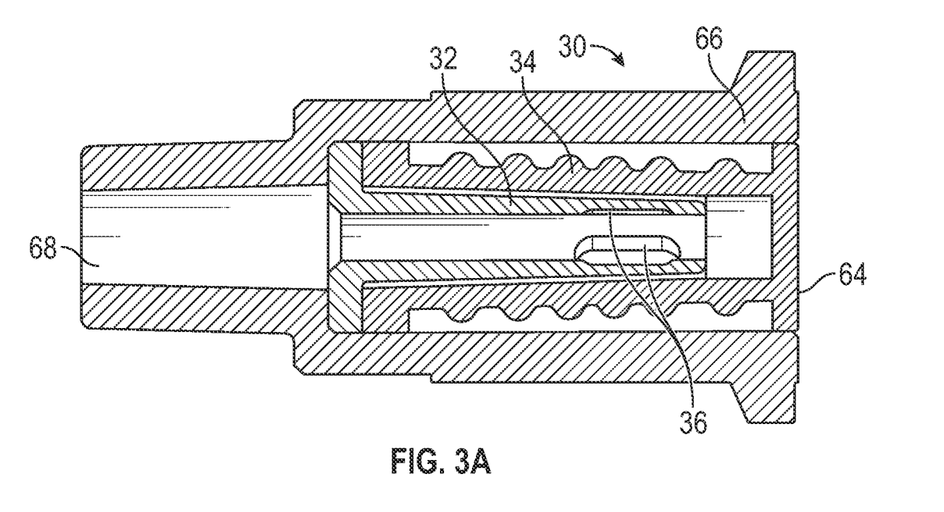
FIG. 3A is a cross-sectional view of an example luer connector, according to some embodiments.
Figure 3B:
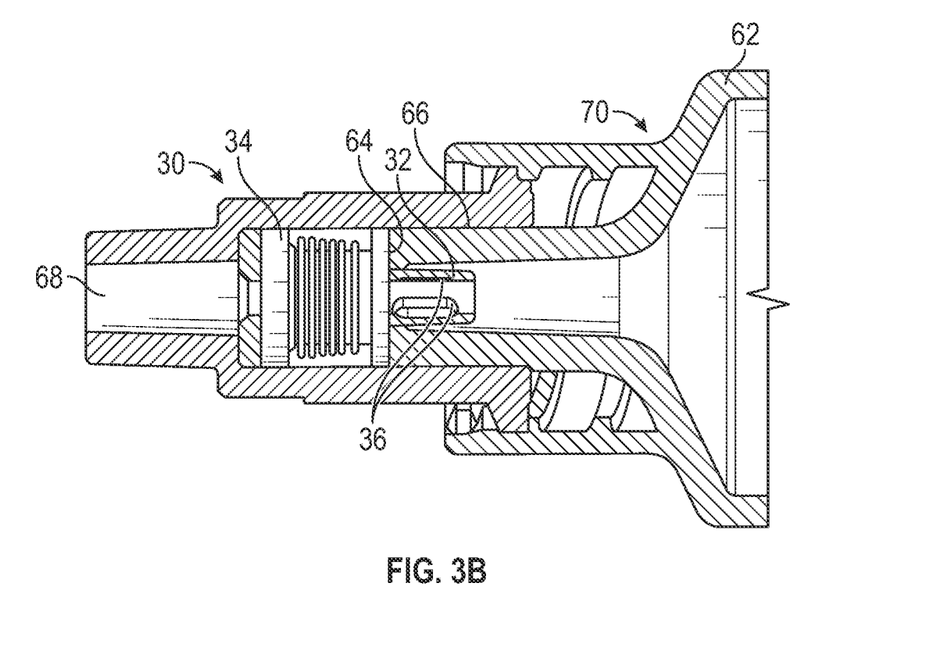
FIG. 3B is a cross-sectional view of the luer connector of FIG. 3A, illustrating an example medical device coupled to a proximal end of the luer connector, according to some embodiments.

Referring now to FIGS. 3A-3B, in some embodiments, after moving the concertinaed tube 24 from the collapsed position to the expanded position, the method may include coupling a medical device 62 to the luer connector 30. In some embodiments, the medical device 62 may include a blood collection device, an infusion device, or an extension set. In some embodiments, the medical device 62 may be coupled to the luer connector 30 when the concertinaed tube 24 is in the collapsed position, and then the concertinaed tube 24 may be moved to the expanded position.

In some embodiments, a proximal end 64 of the slit septum 34 may form a seal with an inner surface 66 of the luer connector 30, which may reduce a dead space within the luer connector 30. In some embodiments, the catheter system 10 may be flushed with only about 2.0 mL due to the reduced dead space. In some embodiments, the catheter system 10 may be flushed with between 2 and 2.5 mL, inclusive. In some embodiments, the proximal end 64 of the slit septum 34 may be easily disinfected with an alcohol swab, for example.

In some embodiments, in response to the medical device 62 being inserted in and/or coupled to the luer connector 30, the medical device 62 may contact the slit septum 34 and compress the medical device 62 in a distal direction to expose the cannula 32. In some embodiments, in response to opening of the slit septum 34, fluid may flow from the medical device 62, distally through the openings 36 of the cannula 32, and out a distal opening 68 of the luer connector 30. In some embodiments, in response to opening of the slit septum 34, blood may flow into the distal opening 68 of the luer connector 30, proximally through the openings 36, and into the medical device 62, which may include the blood collection device.

In some embodiments, a distal end of the medical device 62 may include a luer connector 70 compatible with the luer connector 30. In some embodiments, the luer connector 70 may include a male luer connector and the luer connector 30 may include a female luer connector. In some embodiments, the luer connector 30 may include a 6% luer taper connection (ISO954 compliant) or another suitable percentage. In some embodiments, the luer connector 70 may include a slip male luer connector or a threaded male luer connector. In some embodiments, in response to the luer connector 30 being present within the catheter system 10, no clamping of an extension tube may be needed during coupling and/or uncoupling of the medical device to the catheter system 10.

Figure 4A:
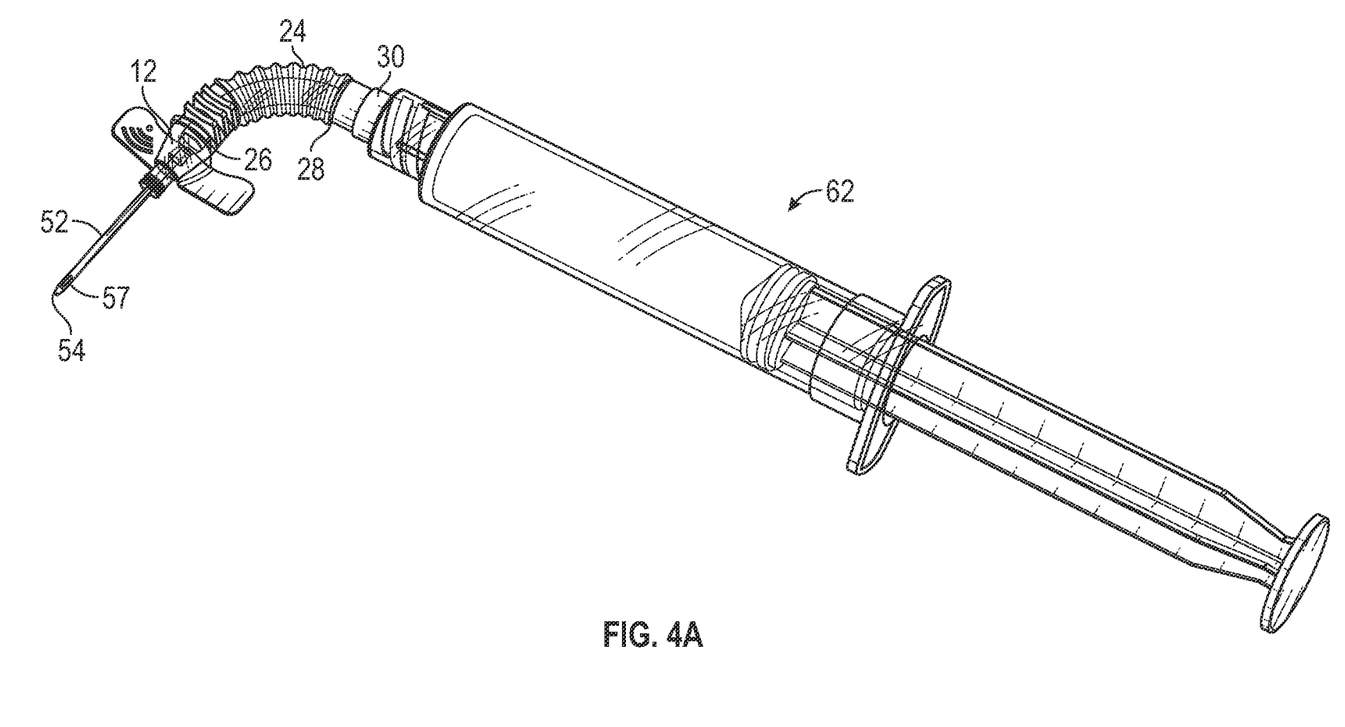
FIG. 4A is an upper perspective view of the catheter system of FIG. 1A, illustrating an example syringe coupled to the proximal end of the luer connector, according to some embodiments.

Referring now to FIG. 4A, in some embodiments, the medical device 62 may include an infusion device, such as, for example, a syringe, which may be coupled to the luer connector 30. In some embodiments, after moving the concertinaed tube from the collapsed position to the expanded position, the infusion device may be activated. In some embodiments, in response to activation of the infusion device or depression of a plunger of the syringe, fluid may flow through the catheter system 10.

Figure 4B:
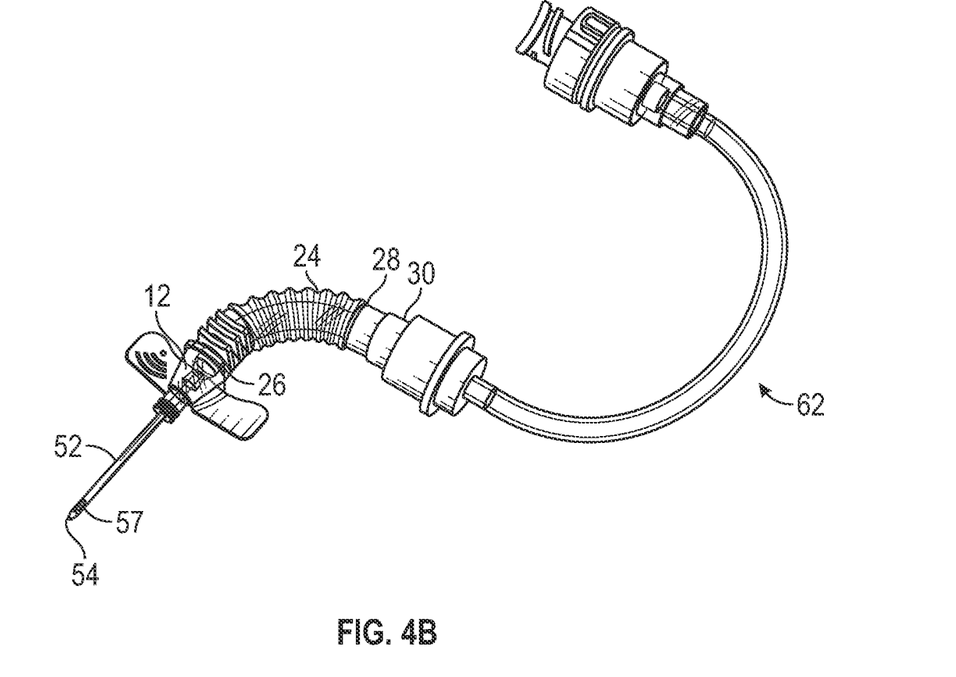
FIG. 4B is an upper perspective view of the catheter system of FIG. 1A, illustrating an example extension set coupled to the proximal end of the luer connector, according to some embodiments.

Referring now to FIG. 4B, in some embodiments the medical device 62 may include an extension set, which may be used to administer a drug to the patient or for another suitable purpose. In some embodiments, the method may include coupling the extension set to the luer connector 30. In some embodiments, after moving the concertinaed tube 24 from the collapsed position to the expanded position, the method may include administering a drug to the patient through the extension set or infusing fluid to the patient through the extension set.

Figure 4C:
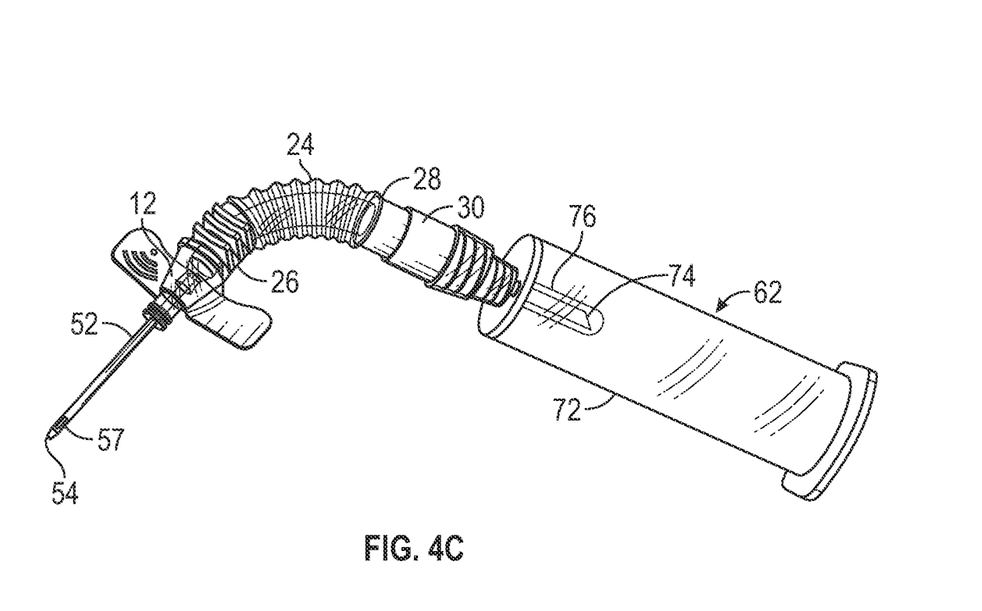
FIG. 4C is an upper perspective view of the catheter system of FIG. 1A, illustrating another example blood collection device coupled to the proximal end of the luer connector, according to some embodiments.

Referring now to FIG. 4C, in some embodiments, the medical device 62 may include a blood collection device, such as a VACUTAINER® (available from Becton Dickinson and Company of Franklin Lakes, New Jersey) or another suitable blood collection device. In some embodiments, the blood collection device may include a holder 72 and a cannula 74 disposed within a pierceable elastomeric sheath 76. In some embodiments, the blood collection device may be configured to receive an evacuated blood collection tube. In some embodiments, after moving the concertinaed tube 24 from the collapsed position to the expanded position, the method may include collecting blood from the patient via the blood collection device.

Figure 4D:
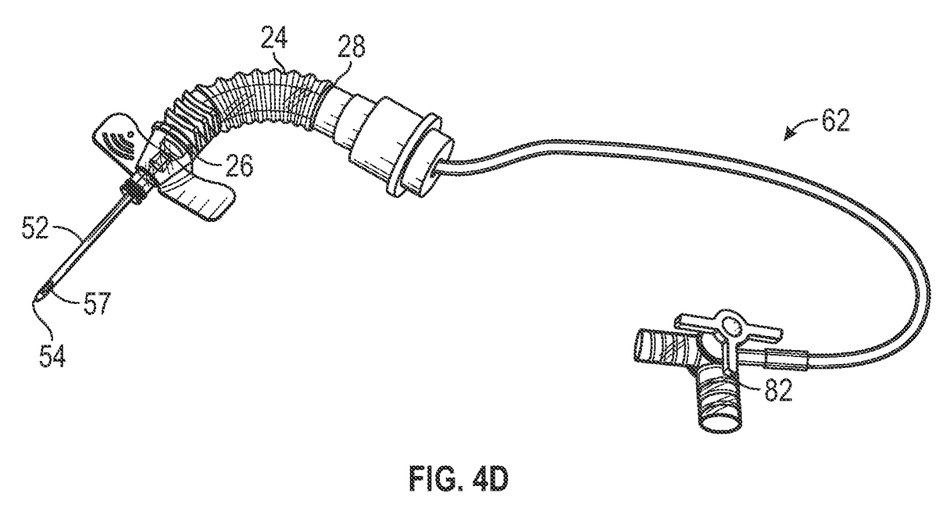
FIG. 4D is an upper perspective view of the catheter system of FIG. 1A, illustrating another example extension set coupled to the proximal end of the luer connector, according to some embodiments.

Referring now to FIG. 4D, in some embodiments the medical device 62 may include another extension set, which may include a stop cock 82. In some embodiments, after moving the concertinaed tube 24 from the collapsed position to the expanded position, the method may include administering a drug to the patient through the other extension set or infusing fluid to the patient through the extension set.

Figure 5A:
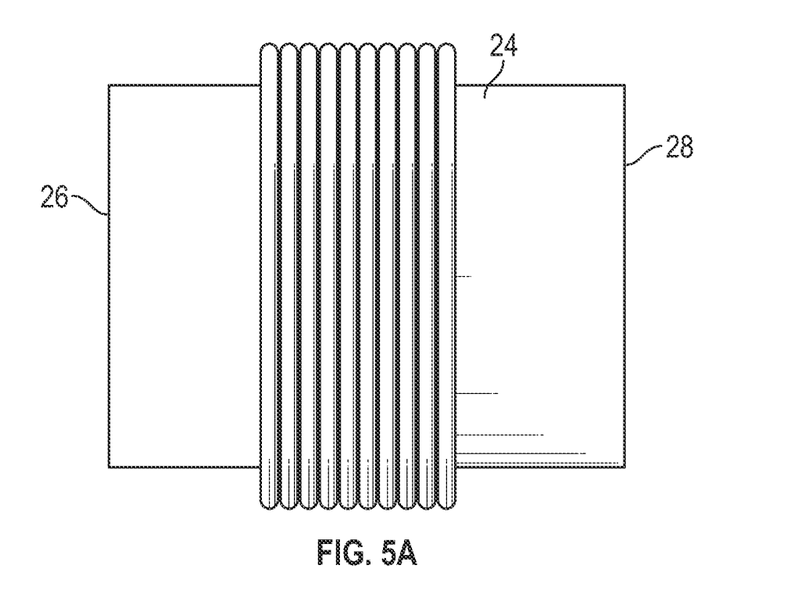
FIG. 5A is an upper perspective view of the concertinaed tube of the catheter system of FIG. 1A in a collapsed position, according to some embodiments.
Figure 5B:
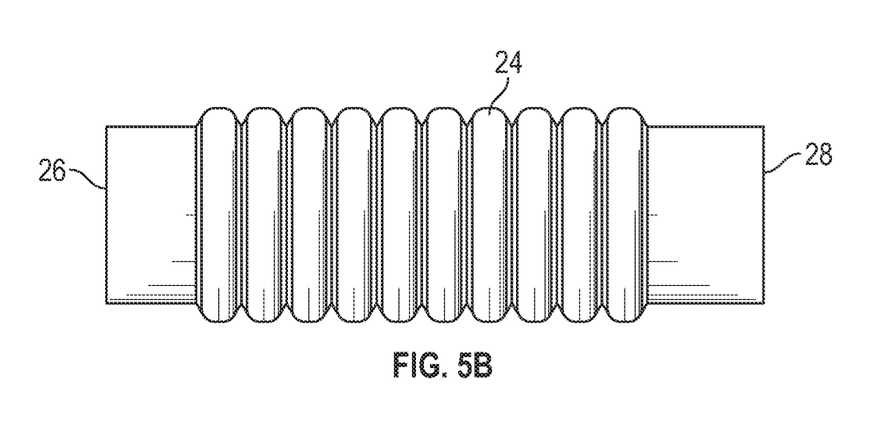
FIG. 5B is an upper perspective view of the concertinaed tube of the catheter system of FIG. 1A in the expanded position, according to some embodiments.
Figure 6A:
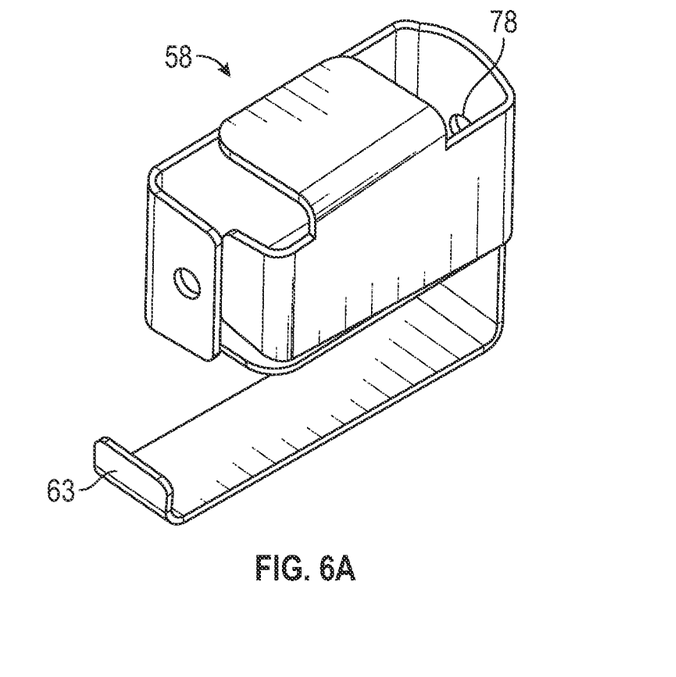
FIG. 6A is an upper perspective view of an example passive safety needle clip of the catheter system of FIG. 1A, according to some embodiments.
Figure 6B:
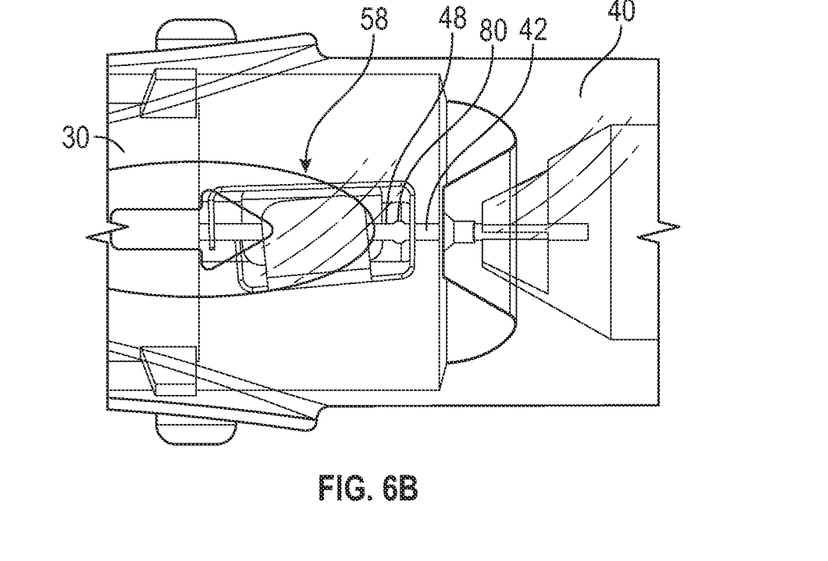
FIG. 6B is a top view of a portion of the catheter system of FIG. 1A, according to some embodiments.
Figure 6C:
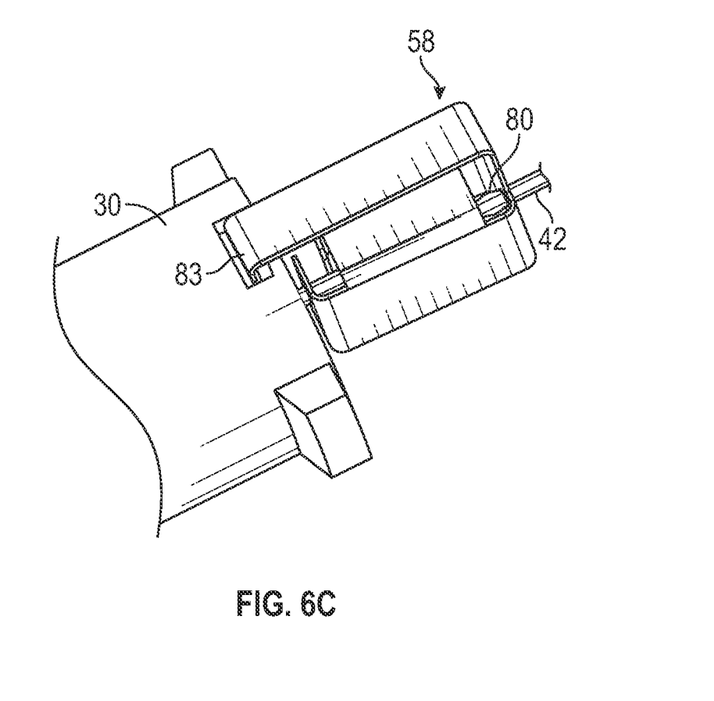
FIG. 6C is a lower perspective view of the passive safety needle clip of FIG. 6A coupled to the luer connector of the catheter system of FIG. 1A, according to some embodiments.
Figure 6D:
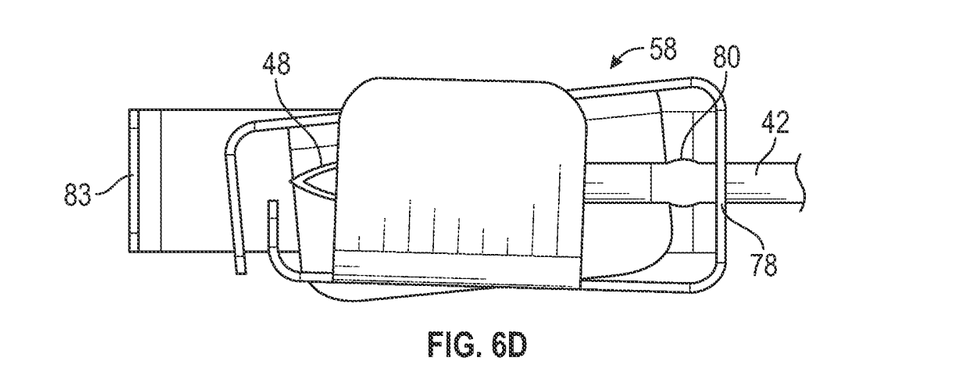
FIG. 6D is a top view of the passive safety needle clip of FIG. 6A shielding an example sharp distal tip of an introducer needle, according to some embodiments.

Referring now to FIGS. 5A-5B, the concertinaed tube 24 is illustrated. In some embodiments, the concertinaed tube 24 may be moved by the clinician between the collapsed position, illustrated in FIG. 5A, and the expanded position, illustrated in FIG. 5B. In some embodiments, the concertinaed tube 24 may be moved automatically from the collapsed position to the expanded position in response to withdrawal of the introducer needle 42. In some embodiments, the concertinaed tube 24 may include multiple folds. In some embodiments, in response to the concertinaed tube 24 moving from the collapsed position to the expanded position, a length of the concertinaed tube 24 may increase. In some embodiments, the concertinaed tube 24 may be flexible and capable of curving. In some embodiments, the concertinaed tube 24 may be constructed of polyvinyl chloride, polytetrafluoroethylene, or another suitable material.

Referring now to FIGS. 6A-6D, the passive needle safety clip 58 is illustrated, according to some embodiments. In some embodiments, the passive needle safety clip 58 may include a V-clip. In some embodiments, the introducer needle 42 may extend through the passive needle safety clip 58. In some embodiments, the passive needle safety clip 58 may include a proximal opening 78. In some embodiments, an outer surface of the introducer needle 42 may include a feature 80, which may include a bump or another suitable feature. In some embodiments, an outer diameter of the feature 80 may be greater than a diameter of the proximal opening 78 such that the feature is prevented from moving proximal to the proximal opening 78. In some embodiments, the passive needle safety clip 58 may include a pawl 83, which may couple to the luer adapter in response to the introducer needle 42 extending through the catheter adapter 12.

All examples and conditional language recited herein are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A catheter system, comprising:
   a catheter adapter, comprising a distal end, a proximal end, and a lumen extending through the distal end and the proximal end;
   a concertinaed tube, comprising a distal end coupled to the proximal end of the catheter adapter and disposed in a collapsed position, wherein the concertinaed tube is movable between the collapsed position and an expanded position;
   a luer connector coupled to a proximal end of the concertinaed tube; and
   a needle assembly, comprising a needle hub and an introducer needle extending distally from the needle hub, wherein the concertinaed tube and the luer connector are disposed within the needle hub, wherein the luer connector is configured to extend through the concertinaed tube in response to movement of the concertinaed tube from the expanded position to the collapsed position such that the luer connector extends distal to the distal end of the concertinaed tube.

2. The catheter system of claim 1, further comprising a catheter extending from the distal end of the catheter adapter, wherein a distal end of the catheter comprises a plurality of side holes.

3. The catheter system of claim 2, wherein the catheter is configured to provide a flow rate of 1.235 mL/hr to 5.400 mL/hr, inclusive.

4. The catheter system of claim 1, further comprising a passive needle safety clip disposed within the needle hub between the luer connector and a proximal end of the needle hub, wherein the introducer needle extends through the passive needle safety clip.

5. The catheter system of claim 4, wherein the passive needle safety clip comprises a proximal opening, wherein an outer surface of the introducer needle comprises a feature, wherein an outer diameter of the feature is greater than a diameter of the proximal opening such that the feature is prevented from moving proximal to the proximal opening.

6. The catheter system of claim 1, wherein in response to the concertinaed tube moving between the expanded position and the collapsed position, a length of the concertinaed tube is reduced by 50% to 70%, inclusive.

7. The catheter system of claim 1, wherein the luer connector comprises a cannula and a slit septum surrounding the cannula, wherein the cannula comprises a plurality of openings.

8. The catheter system of claim 7, a proximal end of the slit septum forms a seal with an inner surface of the luer connector.

9. The catheter system of claim 1, wherein a proximal end of the needle hub comprises a flashback chamber and a hydrophobic filter proximate the flashback chamber.

10. The catheter system of claim 1, where the catheter system has a length of 75 mm or less.

11. The catheter system of claim 1, wherein the catheter adapter comprises one or more push tabs.

12. The catheter system of claim 1, wherein the catheter adapter comprises a first wing and a second wing, wherein the first wing and the second wing extend outwardly from opposite sides of a body of the catheter adapter.

13. The catheter system of claim 1, wherein a proximal end of the needle hub comprises a hydrophobic filter.

14. A method, comprising:
  inserting a catheter system into vasculature of a patient, wherein the catheter system comprises:
    a catheter adapter, comprising a distal end, a proximal end, and a lumen extending through the distal end and the proximal end;
    a concertinaed tube, comprising a distal end coupled to the proximal end of the catheter adapter and disposed in a collapsed position, wherein the concertinaed tube is movable between the collapsed position and an expanded position;
    a luer connector coupled to a proximal end of the concertinaed tube, wherein the luer to movement A connector is configured to extend through the concertinaed tube in response to movement of the concertinaed tube from the expanded position to the collapsed position such that the luer connector extends distal to the distal end of the concertinaed tube; and
    a needle assembly, comprising a needle hub and an introducer needle extending distally from the needle hub, wherein the concertinaed tube and the luer connector are disposed within the needle hub;
  removing the needle assembly from the catheter adapter inserted within the vasculature of the patient;
  after removing the needle assembly from the catheter adapter system, moving the concertinaed tube from the collapsed position to the expanded position.

15. The method of claim 14, further comprising coupling an extension set to the proximal end of the concertinaed tube after moving the concertinaed tube from the collapsed position to the expanded position.

16. The method of claim 15, further comprising administering a drug to the patient through the extension set.

17. The method of claim 14, further comprising coupling an infusion device to the proximal end of the concertinaed tube after moving the concertinaed tube from the collapsed position to the expanded position.

18. The method of claim 14, wherein no priming of the catheter system occurs prior to inserting the catheter system into the vasculature of the patient.

19. The method of claim 14, wherein a single hand is used for inserting the catheter system into the vasculature of the patient.

20. The method of claim 14, wherein in response to removing the needle assembly from the catheter adapter inserted within the vasculature of the patient, a drag force on the introducer needle is less than 1.1 N.

\* \* \* \* \*